United States Patent [19]
Furuya

[11] Patent Number: 5,778,110
[45] Date of Patent: Jul. 7, 1998

[54] TWO-LAYERED STORAGE BAG AND TWO-LAYERED STORAGE BAG ATTACHED TO A DIAPER

[76] Inventor: Kyoko Furuya, 8-18, Haruecho, 2-Chome, Edogawa-ku Tokyo, Japan

[21] Appl. No.: 636,536

[22] Filed: Apr. 23, 1996

[30] Foreign Application Priority Data

Jul. 18, 1995 [JP] Japan ............... 7-008297

[51] Int. Cl.⁶ .................................. B65D 33/24
[52] U.S. Cl. ............... 383/35; 383/87; 604/385.1
[58] Field of Search ............... 383/87, 38, 35; 294/1.3; 604/385.1

[56] References Cited

U.S. PATENT DOCUMENTS

| 2,344,369 | 3/1944 | Salfisberg | 383/38 |
|---|---|---|---|
| 2,709,467 | 5/1955 | Hoeppner | 383/87 |
| 2,994,997 | 8/1961 | Gwinn et al. | 383/87 |
| 3,017,070 | 1/1962 | London | 383/87 |
| 3,230,956 | 1/1966 | Kargul | 604/385.1 |
| 3,369,545 | 2/1968 | Wanberg | 604/385.1 |
| 3,604,423 | 9/1971 | Fraser | 604/385.1 |
| 3,837,696 | 9/1974 | Dahlke | 294/1.3 |
| 3,877,432 | 4/1975 | Gellert | 604/385.1 |
| 3,977,452 | 8/1976 | Wright | 383/87 |
| 4,332,347 | 6/1982 | Clayton | 383/87 |
| 4,493,713 | 1/1985 | Izzo | 604/385.1 |
| 4,808,175 | 2/1989 | Hansen | 604/385.1 |
| 4,923,455 | 5/1990 | Dean et al. | 604/385.1 |
| 5,141,505 | 8/1992 | Barrett | 604/385.1 |
| 5,397,182 | 3/1995 | Gaible et al. | 383/63 |
| 5,413,570 | 5/1995 | Enloe | 604/385.2 |

FOREIGN PATENT DOCUMENTS

| 7-28518 | 5/1995 | Japan . | |
| 7-28528 | 5/1995 | Japan . | |
| 1331643 | 9/1973 | United Kingdom | 383/87 |

*Primary Examiner*—Stephen P. Garbe
*Attorney, Agent, or Firm*—Jacobson, Price, Holman & Stern, PLLC

[57] ABSTRACT

A storage bag to wrap dirty objects such as diapers (including sanitary napkins and the like) without dirtying one's hands. Furthermore, by attaching the bag to a diaper, used diapers can be directly wrapped. The components include a strip of flexible water-resistant sheet material divided into three sections and folded twice in the same direction, and sealed at the sides, and the bottom of the bag attached to the outer upper portion of a diaper.

2 Claims, 3 Drawing Sheets

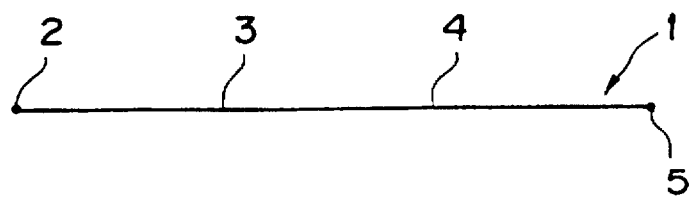
FIG. 1(a)
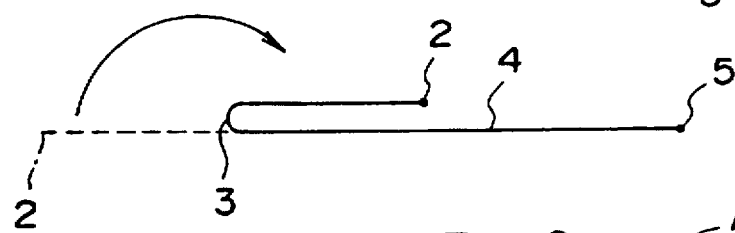
FIG. 1(b)
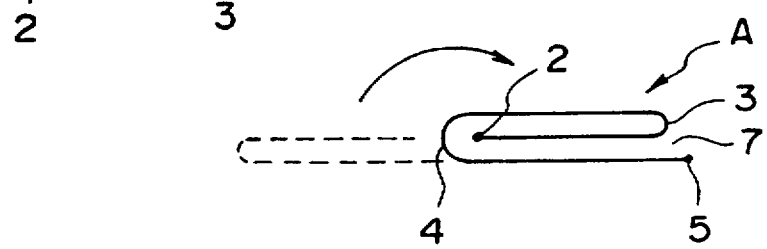
FIG. 1(c)
FIG. 2(a)
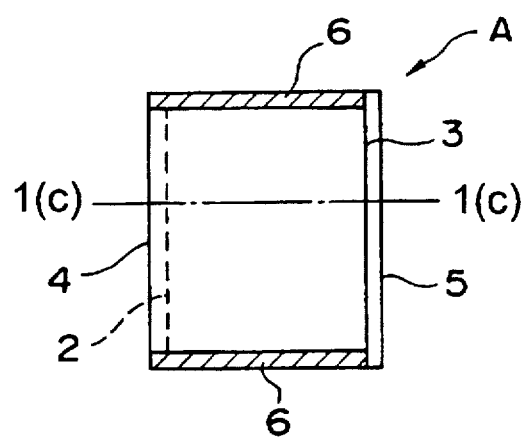
FIG. 2(b)
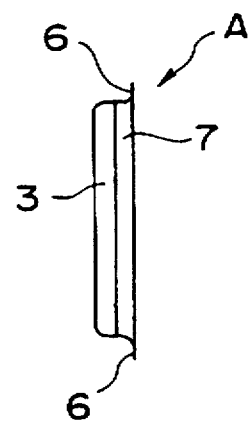

TWO-LAYERED STORAGE BAG AND TWO-LAYERED STORAGE BAG ATTACHED TO A DIAPER

SPECIFICATION

FIELD OF THE INVENTION

The present invention relates to a bag which is used to wrap unsanitary items, such as a diaper (including sanitary napkins) and the like, without soiling the disposer's hands and doing so in a sanitary manner. In extent, the above-mentioned wrapping bag and a diaper is attached together.

BACKGROUND OF THE INVENTION

Disposal of used diapers (and the like) unwrapped is dirty, foul-smelling, and un-sanitary. Furthermore, those that are used by unhealthy patients are contagious by droplet infection and in the process of disposal in an ordinary bag, it is possible to dirty one's hands—especially when folding the object small enough to fit in a bag, that cannot be avoided.

If a diaper (or the like) is put in a bag, it is necessary to seal the opening, but one must supply the string. When one wishes to tie the bag close, the bag must be large enough to be able to tie together. With this invention, used diapers (the diapers related to with this invention includes sanitary napkins and the like) and such dirty objects can be wrapped without dirtying the user's hands, and attaching the bag to a diaper allows for easy wrapping of the diaper. Of course, this invention can also be used to wrap fish or vegetables covered with dirt without dirtying the user's hands.

THE PRIOR ART

Up until now, diapers used by patients in hospitals or those used at home for infants or for the elderly were disposed directly into the waste or disposed wrapped in a bag.

However, as stated previously, disposing used diapers and the like directly is dirty, foul-smelling, and unsanitary. Furthermore, those used by unhealthy patients may be contagious to disease, and when attempting to dispose in a bag, one may dirty their hands—especially when folding the object small to fit in a bag.

BRIEF SUMMARY OF THE INVENTION

The present invention concern a bag which allows for clean and sanitary disposal of diapers (the diapers referred to with this invention includes sanitary napkins and the like) and such dirty objects, and by combining a diaper and the above-mentioned bag, it allows for immediate wrapping in the bag. A strip of flexible impermeable sheet is divided into three sections and folded in the same direction; both sides are then sealed together—this makes up the two-layered or tiered storage bag.

Furthermore, by dividing the strip of flexible impermeable sheet into three sections; folding it in the same direction; and placing the bottom face of the two-layered storage bag on the outside upper portion of a diaper, the used diaper can be enclosed simply and cleanly.

Moreover, in opposite of what is stated above, by placing the upper face of the two-layered bag on the outside upper portion of a diaper, the same results are achieved.

BRIEF DESCRIPTION OF THE DRAWING

FIG. 1 is the explanatory drawing of the steps in making the present invention.

FIG. 2 is the plan surface view and the side elevation view of the two-layered storage bag.

DETAILED DESCRIPTION OF THE INVENTION

Figure 3A:
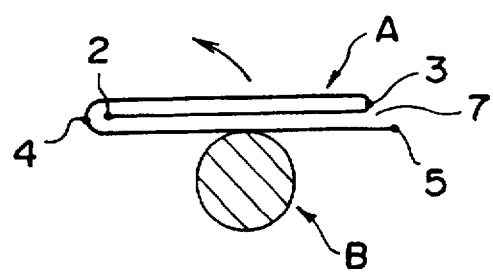
FIG. 3 is explanatory drawing of the steps for usage of the present invention of a two-layered storage bag.

FIG. 1(a)–(c) show the steps in making the present invention of two-layered storage bag. The present invention of a two-layered storage bag, as FIG. 1(a) shows, is made of a strip of flexible impermeable sheet 1, which is folded from the end-side 2 to position 3, where it would be a third of the sheet, as shown in FIG. 1(b), and as FIG. 1(C) shows, it is folded at numeral 4 and 5. Then, as the plan view FIG. 2(a) shows, both ends are sealed at 6.6 and that composes the two-layered storage bag with opening 7. Here, FIG. 1(c) is the cross-sectional view of FIG. 2(a) taken at line X—X, and FIG. 2(b) is the side elevation view of FIG. 2(a).

It will be convenient to keep the length of the divided sheet longer as it is folded further, as FIG. 1 explains, so that the opening can be easily identified.

Figure 3B:
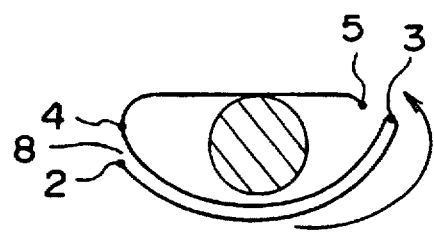
Figure 3C:
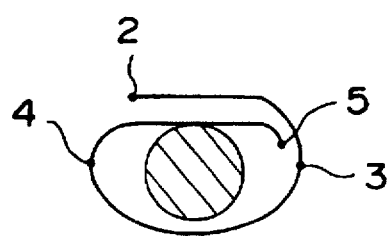

FIG. 3(a)–(c) explains the process of wrapping object B by the two-layered storage bag A. As FIG. 3(a) explains, place the single layered part of the two-layered storage bag (numeral 4-5 of the bag) on object B, grab it by placing hand in opening 7, and then enclose object B by inverting the points 2-3-4, making numeral 4 the axle of the turn (in the direction of the arrow). Then, opening 8 is exposed on bag A (in FIG. 3(b)).

Next, take opening 8 in FIG. 3(b), and likewise with numeral 3, make opening 8 the axle for the turn and wrap the flap around.

Then, numeral 2-3 part of the sheet has overlapped the opening between numeral 3-5, and bag A has completely wrapped object B.

Figure 4A:
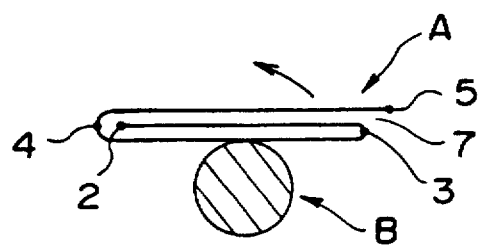
FIG. 4 is explanatory drawing of a different method in usage apart from FIG. 3.
Figure 4B:
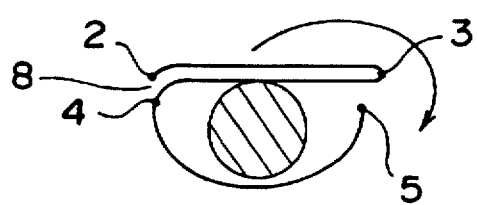
Figure 4C:
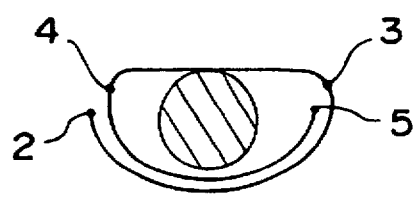

Similarly, FIG. 4 (a)–(c) explains the steps in wrapping object B by the two-layered bag A, but the two-layered side of bag A (numeral 2-3-4 sheet area) contacts object B first.

As FIG. 4(a) explains, the two-layered side of bag A (numeral 4-3-2 of the sheet) is placed on top of object B, and through opening 7, one may grab object B at numeral 4-3-2 and invert the bag, flipping numeral 5-4 over, making numeral 4 the axis of the turn. Then, opening 8 of bag A surfaces, and the bag is in FIG. 4(b).

Next, the opening 8 at FIG. 4(b) is flipped over in the opposite direction from FIG. 4(a), making numeral 3 the axis.

As a result, numeral 2-3 of the sheet encloses the opening between numeral 5-3, and the two-layered bag A has completely wrapped object B. Note here that when enclosing, the turns are not all in same direction.

Figure 5:
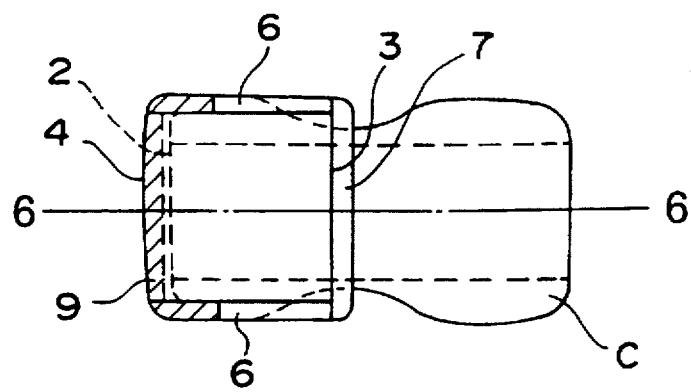
FIG. 5 is a plan view of the two-layered storage bag from underneath.
Figure 6:
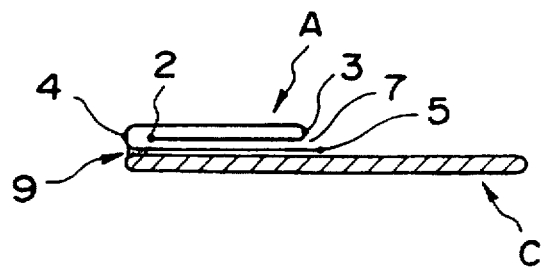
FIG. 6 is a cross-sectional view of FIG. 5 taken at the line X—X.
Figure 7:
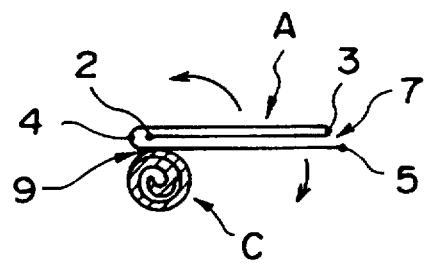
FIG. 7 is the same as FIG. 6 except that the diaper being wrapped is rolled up.

FIG. 5 is the plan view of the outer side of diaper C (the side not contacting the body), where the two-layered bag A is affixed to. FIG. 6 is the cross-sectional of the above taken at line X—X. Again, FIG. 7 shows the same positions as FIG. 6, except that diaper C is rolled.

Now, the method for wrapping in FIG. 4 and the method for wrapping with diaper C attached is mostly identical, so it is abridged here.

FIG. 5 shows the two-layered bag A attached to the outer side (the side not contacting the body) upper portion of diaper C. In order for the sheet to not get in the way of the usage of the diaper, the bottom portion 4 of the bag is affixed to the diaper. In the drawing, the striped zone 9 shows the affixed area. By affixing the bag to the diaper, bag A will not discomfort the user of diaper C, and when the diaper is rolled as in FIG. 7, the side facing the diaper is used to wrap the diaper. Still, it is possible to affix the whole area contacting the diaper, but that may bring about difficulty in wrapping the sheet around the diaper.

The present invention can easily be produced by folding a strip of the sheet in three in the same direction and sealing the sides together. Also, by grabbing the object through the opening and wrapping in order, as explained in FIG. 3 (a)–(c), the object can be wrapped. Furthermore, it is possible to use the bag as explained in the FIG. 4 (a)–(c).

What is claimed is:

1. A storage bag comprising:

a strip of flexible impermeable sheet material having two ends, said strip being folded into three sections to form three walls of the storage bag, with a first section and a second section of the three sections initially forming outermost sections and a third section of the three sections initially located between the first and second sections, a first fold being formed between the first section and the second section, a second fold being formed between the second section and the third section, one of said two ends of said strip being located in the first section and the other of said two ends of said strip being located in the third section, said other end of said strip being located between the first section and the second section and located adjacent to the first fold, said one end of said strip extending beyond the second fold so as to form an identifiable opening for the hand of an individual between the first section and the third section at the second fold, the first section being coextensive with and longer than the second section and the third section and the second section being coextensive with and longer than the third section, and only side edges of said sheet material being sealed at coextensive portions of the first, the second and the third sections so as to allow wrapping of the storage bag two times upon itself around an article with the third section blocking access to the wrapped article within the storage bag and with said one end being located adjacent to said second fold.

2. A storage bag and an article comprising in combination:

a strip of flexible impermeable sheet material having two ends, said strip being folded into three sections to form three walls of the storage bag, with a first section and a second section of the three sections initially forming outermost sections and a third section of the three sections initially located between the first and second sections, a first fold being formed between the first section and the second section, a second fold being formed between the second section and the third section, one of said two ends of said strip being located in the first section and the other of said two ends of said strip being located in the third section, said other end of said strip being located between the first section and the second section and located adjacent to the first fold, said one end of said strip extending beyond the second fold so as to form an identifiable opening for the hand of an individual between the first section and the third section at the second fold, the first section being coextensive with and longer than the second section and the third section and the second section being coextensive with and longer than the third section, side edges of said sheet material being sealed at coextensive portions of the first, the second and the third sections so as to allow wrapping of the storage bag two times upon itself around the article with the third section blocking access to the wrapped article within the storage bag and with said one end being located adjacent to said second fold, and an adhesive strip securing one of the two outermost sections of the sheet material to an outer side of the article prior to the double wrapping of the article, said adhesive strip being located along one of said first and second folds and extending at least partially along both of said side edges of said sheet material.

* * * * *